United States Patent [19]

Javitt et al.

[11] Patent Number: 4,939,134
[45] Date of Patent: Jul. 3, 1990

[54] 26-AMINOCHOLESTEROL AND DERIVATIVES AND ANALOGS THEREOF IN THE REGULATION OF CHOLESTEROL ACCUMULATION IN BODY TISSUE

[75] Inventors: Norman B. Javitt, New York, N.Y.; Stephen R. Wilson, Chatham, N.J.

[73] Assignee: New York University, New York, N.Y.

[21] Appl. No.: 246,444

[22] Filed: Sep. 19, 1988

[51] Int. Cl.$^5$ .............................. A61K 31/56
[52] U.S. Cl. .................................. 514/177; 514/182
[58] Field of Search ................ 514/177, 181, 182

[56] References Cited

U.S. PATENT DOCUMENTS

| | | | |
|---|---|---|---|
| 3,156,619 | 11/1964 | Bertin et al. | 514/182 |
| 3,271,250 | 9/1966 | Kaazawa et al. | 514/177 |
| 3,291,690 | 12/1966 | Bertin et al. | 514/182 |
| 3,839,565 | 10/1974 | Saltzman | 514/177 |
| 4,427,668 | 1/1984 | Javitt | 514/182 |

OTHER PUBLICATIONS

CA 98:103618k (1983).
CA 94:27444a (1981).
CA 82: 13692v (1975).
CA 79:144832b (1973).
CA 110:5143y (1988).
CA 91:141094z (1979).

*Primary Examiner*—Joseph A. Lipovsky
*Attorney, Agent, or Firm*—Darby & Darby

[57] ABSTRACT

This invention relates to cholesterol synthesis and to the accumulation and regulation of cholesterol levels in body tissue. More specifically, the invention provides that the compound 26-aminocholesterol,

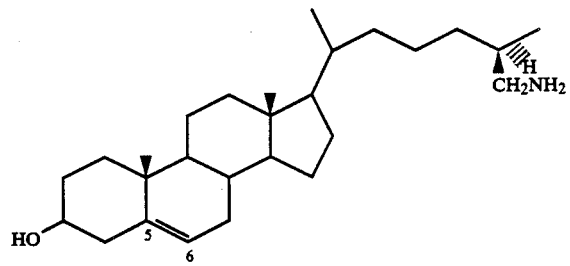

and analogs and derivatives thereof, exhibit biological activity as a potent inhibitor of cholesterol synthesis and/or cholesterol accumulation in body tissue. The compounds strongly inhibit of the enzyme HMGCoA reductase and low density lipoprotein accumulation by non-hepatic cells. Surprisingly, it has been discovered that 26-aminocholesterol is selective for fibroblast (plasma) cells, and has little or no effect on hepato (liver) cells. Therapeutic compounds according to the invention include substituted or unsubstituted sterols of the formula:

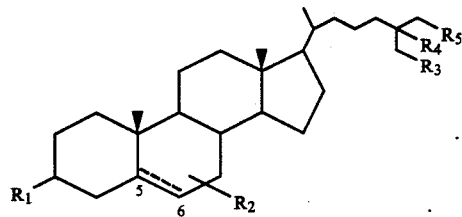

wherein the carbon atoms at positions 5 and 6 of the sterol are one of saturated and unsaturated, $R_1$ is one of a 3-hydroxyl group and a 3-keto group, $R_2$ is one of a hydroxyl group and a keto group, and wherein at least one of $R_3$, $R_4$ and $R_5$ is an amino group and the others are each selected from the group consisting of hydrogen and an amino group.

22 Claims, No Drawings

26-AMINOCHOLESTEROL AND DERIVATIVES AND ANALOGS THEREOF IN THE REGULATION OF CHOLESTEROL ACCUMULATION IN BODY TISSUE

This invention relates to the regulation of cholesterol levels in body tissue. More specifically, the invention provides that the compound 26-aminocholesterol and certain of its derivative and analogs exhibit a unique biological activity as a potent downregulator of LDL receptors in cells and tissues outside the liver, thus preventing cholesterol accumulation in body tissue. Surprisingly, it has been discovered that 26-aminocholesterol is selective for fibroblast (plasma) cells, and has little or no effect on hepato (liver) cells. Thus, the invention relates to the prevention of atherosclerosis, apparently by blocking the buildup of cholesterol in the tissues outside the liver. In addition, the inventive compounds inhibit cholesterol synthesis by tissue cells. These downregulation and synthesis inhibition effects have been observed only in non-hepatic cells, and therefore the compound do not interfere with normal cholesterol metabolism by the liver. Unlike other compounds that primarily affect cholesterol synthesis in the liver, which lowers blood plasma cholesterol, the present invention describes novel compounds that protect cells from the accumulation of cholesterol irrespective of the plasma cholesterol level. The compounds can be used therapeutically, either alone or in combination with other drugs and/or pharmaceutical carriers, as a means for regulating cholesterol levels and preventing and treating diseases related to cholesterol build-up.

This work was supported by the National Institute of Health, under Grants DK32995 (N.B.J.) and GM32400 (S.R.W.). Through these grants, the U.S. Government has rights in this invention.

BACKGROUND OF THE INVENTION

Cholesterol is the major steroid constituent of animal tissue, and is a normal component of plasma and essentially all cell membranes. Cholesterol is a hydrophobic hydrocarbon compound with a reactive hydroxyl group. It is a 3-hydroxy sterol (having a perhydro-1,2-cyclopentenophenanthrene ring system skeleton) with an aliphatic side chain at position 17. In theory, it plays a major role in regulating the fluidity and permeability of the cell membrane, by forming an intercalated structure among the membrane phospholipids.

Cell membranes can experience transitions between a fluid-like consistency and a gel-like consistency, a phenomenon that is highly temperature sensitive. As a result, a membrane that is relatively fluid at 37° C. can rapidly gel at temperatures only a few degrees lower.

In theory, cholesterol can prevent a temperature induced fluid to gel transition (a reduction in fluidity) by preventing the fatty acyl chains of the membrane lipids from binding with each other. This is achieved through its orientation within the membrane structure: the polar hydroxyl group of cholesterol is grounded toward the aqueous surface of the membrane and the polar heads of the membrane phospholipids, while the steroid ring is interposed between the fatty acyl side chains and keeps them apart. Darnell, et al., *Molecular Cell Biology*, Scientific American Books (New York: 1986), p. 576–577. Cholesterol can be obtained from the diet or synthesized in the liver. It can also be manufactured within the cell, if needed, but in practice most cells receive their cholesterol externally. Cholesterol synthesis occurs according to an enzyme-mediated biosynthetic pathway, in which the rate limiting enzyme is believed to be hydroxymethylglutaryl-Co-A reductase ("HMG CoA reductase"). See, for example, Javitt, U.S. Pat. No. 4,427,668. This enzyme catalyzes the formation of mevalonic acid, a cholesterol precursor, from hydroxymethyl glutaric acid. In theory, cholesterol production can be regulated by interfering with HMG CoA reductase. Goodman & Gilman, *The Pharmacological Basis of Therapeutics*, 7th ed., MacMillan (New York: 1985), pp. 841–843; Kandustsch et al., *Science*, 201, 498 (1978).

Cholesterol is insoluble in body fluids, and therefore must be transported through the bloodstream by a carrier. Perhaps the most clinically significant carrier is low-density lipoprotein (LDL), which can be envisioned as an apolar core of cholesterol (as a fatty acid ester) encapsulated within a spherical phospholipid monolayer membrane. The LDL membrane is embedded with a specific hydrophobic protein. Serum LDL particles have a diameter of from 20 to 25 nm, and are the major source of cholesterol for most cells. Darnell, supra., p. 648–650.

Accordingly, most cells manufacture specific receptors that will bind LDL to the cell membrane. Cholesterol can be internalized by cells bearing appropriate receptors, such as fibroblast cells, by receptor-mediated endocytocis. This is a process in which LDL forms a ligand-receptor complex by binding to the LDL receptor on the exterior of the cell membrane. Through a complex mechanism, LDL is transported across the membrane as a ligand-receptor vesicle, the receptor is recycled (in budded vesicles) to the membrane surface, and LDL is transported to the lysosomes (still in vesicles), where it is degraded to release cholesterol for use in the cell membrane. Id. Thus, it is believed that cholesterol accumulation (cellular uptake) and synthesis can be regulated by interfering with LDL binding.

The excessive accumulation of cholesterol has been implicated as the prime causative factor in a number of diseases. In particular, elevated concentrations of cholesterol can cause and/or hasten atherosclerosis, which is characterized by an abnormal hardening and thickening of the arterial walls due to the accumulation and deposition of fatty materials, including cholesterol. This, in turn, can lead to thrombosis and infarction. Accordingly, there is a need for means to therapeutically regulate cholesterol levels, especially when those levels become abnormally high. See, for example, Goodman & Gilman, pp. 827, 832.

Representative of known drugs that are currently in use are mevinolin and cholestyramine, which cause the upregulation of LDL receptors in the liver. Mevinolin, which is an allosteric inhibitor of HMG CoA reductase, achieves this regulation effect by inhibiting cholesterol synthesis in the liver. This stimulates increased LDL receptor activity in the liver, causing hepatic uptake of cholesterol, which in turn reduces plasma cholesterol. Cholestyramine increases the need for bile acid synthesis from cholesterol in the liver, which in some individuals will result in upregulation of LDL receptors. Once again, this reduces plasma cholesterol. The primary effect of both compounds is therefore limited to the liver. The known compounds are not intended to and do not significantly effect cells outside the liver. A strategy targeted for the liver is effective using the known compounds because, unlike other cells, liver cells can uniquely metabolize (and remove) cholesterol to bile acids. Indeed, compounds such as mevinolin would have a detrimental effect on the accumulation of tissue cholesterol if targeted on cells outside the liver, since the compound would upregulate the LDL receptors and would cause rather than reduce cholesterol accumulation.

Another known compound is 26-hydroxycholesterol, which is the subject of commonly owned U.S. Pat. No. 4,427,668, ("the '668 patent") the disclosure of which is hereby incorporated by reference. See also, Javitt et al., *J. Biol. Chem*, 256, 24: 12644–12646 (1981); Brooks et al., *Biochem Soc. Trans.*, 11: 700–701 (1983); Koopman et al., *J.Chromatogr.*, 416: 1–13 (1987); Easterman and Javitt et al., *J. Lipid Res.*, 24: 1304–1309 (1983); and Taylor et al., *J. Biol. Chem.*, 259, 20: 12382–12387 (1984).

The '668 patent suggests that certain derivatives and analogs of 26-hydroxycholesterol might be worthy of investigation as regulators of cholesterol production. By "derivative" and "analog" the patent expressly contemplates fatty acid mono and di-esters, sulfates, carbonates, glucuronides and ether or fluoro substitutions of 26-hydroxycholesterol. The patent does not disclose that any particular derivative or analog in fact exhibits biological activity as an inhibitor of cholesterol, HMG CoA reductase or LDL binding. The patent merely suggests a possible avenue for research. Moreover, there is no suggestion that any cholesterol reducing compound is a downregulator of LDL receptor binding or can be targeted specifically for non-hepatic (e.g., fibroblast) cells.

It should also be noted that there is no reliable correlation between liver or plasma cholesterol levels and the amount of HMG CoA reductase and LDL receptor binding. For example, the known drug mevinolin has been observed to inhibit hepatic cholesterol synthesis even though it increases the amount of HMG CoA reductase. The enzyme is less active in the presence of the drug, which is believed to modify mevinolin's three-dimensional conformation. From cell culture studies it is known that this drug (and others) also upregulates LDL receptors in fibroblasts and other non-hepatic cells. In contrast, 26-aminocholesterol and the derivatives and analogs herein inhibit HMG CoA reductase activity in fibroblasts and reduces LDL binding, thereby decreasing the rate at which tissue cells can produce and accumulate cholesterol. See also, Javitt et al., "Cholesterol metabolism: use of D$_2$O for determination of synthesis rate in cell culture," *J.Lipid Res.*, 26: 950–954 (1985); Lorenzo et al., "Regulation of low density lipoprotein metabolism by 26-hydroxycholesterol in human fibroblasts," *FEBS Letters*, 218: 1, 77–80 (1987).

The drugs currently in use for the inhibition of cholesterol synthesis have an impact primarily on the liver, and are believed to function by causing upregulation of the LDL receptors of the liver (to increase liver uptake of cholesterol and decrease serum levels) or by inhibiting HMG CoA reductase, so that cholesterol production is reduced. The present compounds produce observably different results, in that LDL receptor binding of tissue cells is downregulated, while hepatic cells are not affected.

SUMMARY OF THE INVENTION

It has now been discovered that the compound 26-aminocholesterol, and certain amino-substituted analogs and derivatives thereof, especially those with a deoxygenated aliphatic chain that is polar and/or basic in character, are potent inhibitors of cholesterol accumulation and synthesis. In particular, it has been discovered that 26-aminocholesterol selectively inhibits and reduces LDL binding to the LDL receptors of fibroblast cells, while having little or no effect on hepatoma (HepG2) cells. In addition to downregulating LDL receptor binding, the compound also downregulates cholesterol synthesis by non-hepatic cells.

The present invention differs dramatically from the known drugs, because it specifically targets non-liver cells. Instead of upregulating hepatic LDL receptors and increasing the capacity of the liver to remove plasma cholesterol, 26-aminocholesterol lowers the amount of cholesterol in tissue cells, apparently by downregulating their LDL receptors and simultaneously reducing their capacity to synthesize cholesterol. In this way, it is possible to protect cells from high levels of plasma cholesterol, so that its accumulation in body tissue is markedly reduced. It is believed at this time that 26-aminocholesterol does not effect liver cells because the compound is metabolized very rapidly once it reaches the liver.

Accordingly, the present invention is concerned with reducing accumulation of cholesterol in body tissues and its synthesis and distribution in body tissue. More particularly, it is an object of the present invention to reduce abnormally high levels of serum cholesterol, and to prevent and treat atherosclerosis and other diseases associated with excessive cholesterol accumulation, by administering an effective cholesterol-reducing amount of 26-aminocholesterol or derivatives and analogs thereof.

Another object of the invention is to provide a method for regulating cholesterol synthesis and accumulation in the body.

Another object of the invention is to provide compounds which can be administered to humans afflicted with excessive accumulation of serum cholesterol, for the purpose of reducing the rate of cholesterol accumulation.

Still another object of the invention is to provide a compound and method for selectively regulating cholesterol accumulation in body tissue, without interfering with cholesterol synthesis and metabolism in the liver.

A further object of the invention is to provide pharmaceutical preparations containing a compound or compounds of the invention in an amount sufficient for use in one or more of the embodiments of this invention.

Other objects of the invention will be apparent to skilled practitioners from the detailed description of the invention provided below.

DETAILED DESCRIPTION OF THE INVENTION

The compound 26-aminocholesterol,

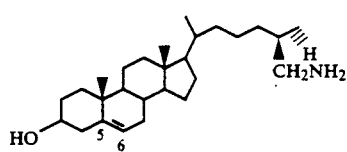

I has been found to influence de novo cholesterol synthesis and low-density lipoprotein (LDL) binding in human serum fibroblasts, while having no impact on human hepatocytes. Thus, it appears that the compound is either selective for the synthesis and accumulation of cholesterol in fibroblast cells, or is selectively ignored or avoided by liver cells, perhaps through rapid metabolic decomposition in the liver. These findings also suggests that the biosynthetic pathways for cholesterol production in serum and in the liver may be different, and may employ different mechanisms of action.

Preparation of 26-Aminocholesterol

25(R), 26-aminocholesterol was prepared by lithium aluminum hydride (LAH) reduction of 25(R), 26-azidocholesterol 3-acetate synthesized from 26-tosylcholesterol 3-acetate. See, Tschesche et al., *Chem Ber.*, 112: 2680–2691 (1979); and Seo, et al., *J. Chem. Soc. Perkin Trans. I*, 411–414 (1986).

The 26-azidocholesterol 3-acetate starting material was obtained by dissolving 397 mg (0.663 mmoles) of 26-tosyl-cholesterol 3 acetate in 25 ml of anhydrous dimethyl formamide (DMF) in a 100 ml three-neck flask fitted with a stir bar and a nitrogen bubbler. Then, 56 mg (0.853 mmoles) of sodium azide and 1 ml of water was added, and the solution was heated to between 90° and 100° C. After two hours, the solution was cooled to room temperature an poured into a 500 ml separatory funnel containing 200 ml of water. The aqueous solution was extracted three times with diethyl ether and the pooled extracts were washed with saturated sodium chloride solution and dried. Rotoevaporation yields 254 mg of 26-azidocholesterol 3-acetate as a white powder (81.6% yield) that was subsequently recrystallized in ethanol to yield 126 mg of white waxy crystals. The melting point of this intermediate product was 90°–90.5° C.

NMR analysis revealed the following, in ppm: 0.701 (3, s, C-18 methyl), 0.941 (3, d, C-27 methyl, J=6.6 Hz), 0.970 (3, d, C-21 methyl, J=6.6 Hz), 1.042 (3, s, C-19 methyl), 2.058 (3, s, methyl of acetate on C-3), 3.1765 (3, multiplet ABX, J=38.17 Hz, J=11.89 Hz, J=5.97 Hz), 4.626 (1, m, C-3), 5.398 (1, d, C-6, J=4.50 Hz). IR analysis, (1/cm) provided: 2950 (C—H), 2100 (N—N), 1725 (C=O), 1250 (N—N) and 1050 (C—O).

The 26-azidocholesterol 3-acetate (100 mg, 0.213 mmoles) was dissolved in 20ml of anhydrous diethyl ether in a 50 ml three-neck flask fitted with a stir bar and a nitrogen bubbler. LAH (20 mg, 0.527 mmoles) supplied by Aldrich (95%) was added directly to the flask and the exothermic reaction was refluxed for one hour. The reaction mixture was quenched with water and was poured into a 100 ml separatory funnel. The aqueous layer was removed and the ethereal layer was washed with saturated sodium chloride solution and dried. Rotoevaporation resulted in 70 mg of 26-aminocholesterol as a crude white powder (81.9% yield). This was purified via Flash chromatography (93:7:1 chloroform::ethanol:29% ammonium hydroxide, using 230–400 mesh silica gel supplied by Merck) to afford 48 mg of the desired final product, 26-aminocholesterol. The melting point of the product was 149°–152° C. (148°–151° C., see, Tschesche, supra).

NMR analysis revealed the following, in ppm: 0.669 (3, s, C-18 methyl), 0.875 (3, d, C-27 methyl, J=6.6 Hz), 0.906 (3, d, C-21 methyl, J=6.6 Hz), 0.999 (3, s, C-19 methyl), 2.528 (3, 2, m, C-26), 3.499 (1, m, C-3), and 5.342 (1, d C-6 proton, J=5.1 Hz). IR analysis, (1/cm) provided: 3600 (N—H), 2950 (C—H), and 1050 (C—O).

Melting points were determined in open capillary tubes on a Thomas-Hoover Capillary melting point apparatus and uncorrected. NMR spectra (CDCL$_3$) were run on a Nicolet QE-300 spectrometer. IR spectra were obtained on a Matteson Polaris FTIR instrument. All reagent grade chemicals, except as otherwise noted, were obtained from Aldrich Chemical Company.

Preparation of Fibroblasts and HepG2 Cells

Normal LDLR(+) human fibroblasts (GM3440) were obtained from the National Institute of General Medical Sciences Human Genetic Cell Repository. Stock fibroblast monolayers were maintained in T-75 disposable Nunc flasks, in a medium comprising 10 ml of MEM (Eagle's Minimum Essential Medium with Earl's salts, pH 7.4) supplemented with 10% (v/v) fetal bovine serum (FBS), 2% (v/v) non-essential and essential amino acids, 1% (v/v) MEM vitamins, 1% L-glutamine (292 ug/ml), 1% penicillin (100 U/ml)-streptomycin (100 ug/ml). The fibroblast stock was maintained at 37° C. in a humidified atmosphere of 5% $CO_2$ and 95% air.

HepG2 cells were obtained from Dr. Barbara Knowles of the Wistar Institute, Pennsylvania. The HepG2 stock monolayers were maintained under the same conditions as the fibroblast monolayers, in a medium comprising MEM supplemented with 10% heat-inactivated FBS, and 1% (v/v) each of penicillin-streptomycin solution, non-essential and essential amino acids, and L-glutamine.

The medium was routinely changed every 3–4 days and the cells were massaged (1:3) every 7 days. The ingredients for these media were supplied primarily by Gibco Chemical Co.

For experiments using fibroblasts, confluent stock cultures (5–18 passages) were washed once with Dulbecco's PBS (phosphate buffered saline) prior to the addition of 3 ml aliquots of experimental MEM containing 25% (v/v) $D_2O$, 9% (v/v) dilapidated FBS, 1% FBS (v/v), 1% MEM vitamins and L-glutamine, and 2% of essential and non-essential amino acids and 20 mM HEPES buffer.

For experiments using HepG2 cells, confluent stock monolayers were washed once with Dulbecco's PBS, dissociated with 0.05–0.02% trypsin-EDTA followed by treatment with deoxyribonuclease I (0.1%), and were seeded (3.0×10$^6$) under identical conditions. The experimental MEM contained 25% (v/v) $D_2O$, 9% (v/v) delipidated FBS, and 1% (v/v) each of heat-inactivated FBS, penicillin-streptomycin, essential and non-essential amino acids, L-glutamine and 20 mM HEPES.

The fibroblast and hepatoblastoma cells were cultured in media containing 25% $D_2O$ and 1% FBS in order to determine de novo cholesterol synthesis under conditions that permit receptor mediated cholesterol transport, according to the method of Easterman & Javitt et al., *J. Lipid Res.*, 26: 950–954 (1985). Dish cultures of each cell type were prepared, and 26-aminocholesterol, dissolved in N,N-dimethylformamide (DMF, 9 ul per dish, 0.3% v/v) was added to each culture. The cells were then grown to confluence (96 hours, day 5). No effect on cell growth was observed at the maximum concentrations tested. Duplicate or triplicate dishes containing 9 ul of DMF, but without 26-aminocholesterol, were used as controls.

The effect of 26-aminocholesterol on LDL receptor binding, de novo cholesterol synthesis, and distribution of total and esterified cholesterol were determined at this stage of growth.

Assay for Total LDL Binding to Culture Cells

LDL (d, 1.019–1.03) was isolated by sequential preparative ultracentrifugation of normal human plasma, using solid KBr for density adjustment, according to the methods of Havel et al., *J. Clin. Invest.*, 34: 1345–1353 (1955) and Radding & Steinberg, *J Clin. Invest.*, 39: 1560–1569 (1960). The isolated LDL was then iodinated with $^{125}$INa by the monochloride procedure of McFarlane, *Nature*, 102: 53 (1958), as modified for lipoproteins according to Bilheimer et al., *Biochim. Biophys. Acta.* 260: 212–221 (1972). To remove free iodine, the LDL preparation was subjected to column chromatography on a Sephadex G-25M disposable mini-column (Pharmacia PD-10) and was dialized against 0.15 M NaCl and 0.3 nM EDTA, pH 7.4. The specific activity of all LDL preparations ranged between 160–300 cpm/mg of LDL proteins. $^{125}$I-LDL was stored at 4° C. and was sterilized by filtration through a 0.45 um membrane just prior to incubation with the treated fibroblast and hepatoblastoma cell cultures and control cultures.

For binding studies, a fixed concentration of 10 ug/ml of $^{125}$I-LDL was added directly to the monolayers of the confluent culture medium (at or near the 96th hour) and incubation was continued for a further 4 hours at 37° C. for fibroblasts and 4° C. for HepG2 cells. After this incubation, the culture dishes were placed on ice, the medium was removed, and the cell monolayers were washed as described in Goldstein & Brown, *J. Biol. Chem.*, 249: 5153–5162 (1974). The monolayers were then scraped off the dishes with a teflon policeman and were solubilized with 1 ml of 0.1 N NaOH.

Cell-associated radioactivity was measured in a Packard auto gamma scintillation spectrometer Model 5160, and cell protein was measured by the method of Lowry et al., *J. Biol. Chem.*, 193: 265–275 (1951), using bovine serum albumin as a standard. Total $^{125}$I-LDL binding was expressed as the mass of $^{125}$I-LDL (mg) per mg of cell protein.

Cholesterol Assays

After 96 hours of incubation, medium was removed from the cell cultures, and the cells were washed with Dulbecco's PBS and were harvested with 0.05% trypsin - 0.02% EDTA. The protease was deactivated with an equivolume aliquot of soybean trypsin inhibitor, and the resulting cell suspension was centrifuged for 5 minutes at 500xg. An internal standard of 5B-cholestan-3B-ol was added to the pellets prior to extraction with an 8:4:3 chloroform:methanol:water Folch mixture, as described in Folch et al., *J. Biol. Chem.*, 266: 497–509 (1957). An aliquot of the extract was blown to dryness under nitrogen and silylated with 2:1:1 MSTFA (a sylated reagent supplied by Pierce Co.): toluene:-pyridine. Free cholesterol was determined by gas-liquid chromatography (GLC) on a Perkin-Elmer capillary gas-liquid chromatography model 8320 fitted with a 20 m DE-1 methylsilicon glass column (Supelco). The remaining extract was dried and saponified with 2% ethanolic KOH at 80° C. for one hour. The 26-aminocholesterol was then re-extracted and total cholesterol was measured by GLC after silylation. Cholesterol ester was calculated as the difference between the total and free cholesterol determinations. Newly synthesized cholesterol was determined by GLC-MS isotope mass ratios, using a Hewlett-Packard GC-MS spectrometer model 5890 fitted with DB-1 methyl silicon 0.18 i.d. 20 m glass column (Supelco), according to the method of *J. Lipid. Res.*, 26: 950–954, *supra*.

Comparative Assays

For purposes of comparison, $^{125}$I-LDL and cholesterol assays were also conducted in cultures prepared according to the above methods, but incubated with 26-hydroxycholesterol in one set of experiments and with the sterol 26-thiacholesterol in another set of experiments. These sterols were obtained according to known methods, similar to those described above for 26-aminocholesterol.

Experimental Results

The results of the LDL binding and cholesterol experiments are shown in the following tables, with TABLE 1 showing the effect of the tested sterols on LDL binding and cholesterol synthesis in fibroblast cells, and TABLE 2 showing the results for HepG2 cells.

TABLE 1

LDL BINDING AND CHOLESTEROL IN HUMAN FIBROBLASTS
Effect of 26-NH$_2$, 26-SH and 26-OH cholesterol on Total
Cell Cholesterol, Percent Esterified Cholesterol, De
Novo Cholesterol Synthesis, and $^{125}$I-LDL Binding to
LDLR (+) Human Fibroblasts (n = 3)

26-NH$_2$  26-Aminocholesterol
26-OH     26-Hydroxycholesterol
26-SH     26-thiacholesterol

| STEROL | TOTAL CHOLESTEROL ug cholesterol per mg cell protein | % ESTER | % DE NOVO | $^{125}$I-LDL BINDING ug LDL protein per mg cell protein |
|---|---|---|---|---|
| none | 32.1 +/− 1.2 | 28.5 | 19.0 | 49.7 +/−0.9 |
| 26-OH | | | | |
| 0.625 uM | 24.7 +/− 2.8 | 28.7 | 3.9 | 22.0 +/− 2.4 |
| 26-NH$_2$ | | | | |
| 0.156 uM | 27.9 +/− 5.3 | 26.4 | 16.7 | 29.6 +/− 1.1 |
| 0.312 uM | 31.5 +/− 6.1 | 18.6 | 10.0 | 22.6 +/− 5.4 |
| 0.625 uM | 20.3 +/− 6.4 | 6.4 | 2.7 | 13.3 +/− 1.6 |
| 26-SH | | | | |
| 5.0 uM | 26.0 +/− 1.7 | 13.6 | 27.8 | 37.9 +/− 1.8 |
| 10.0 uM | 31.3 +/− 4.5 | 31.1 | 21.9 | 25.7 +/− 0.7 |
| 20.0 uM | 26.1 +/− 1.0 | 33.1 | 13.6 | 35.7 +/− 4.8 |

TABLE 2

LDL BINDING AND CHOLESTEROL
IN HUMAN HEPG2 HEPATOCYTES
Effect of 26-NH$_2$, 26-SH and 26-OH cholesterol
on Total Cell Cholesterol, De Novo Cholesterol Synthesis, and $^{125}$I-LDL Binding to HepG2 Cells (n = 3)

| STEROL | 26-NH$_2$ 26-Aminocholesterol<br>26-OH 26-Hydroxycholesterol<br>26-SH 26-thiacholesterol<br>TOTAL CHOLESTEROL<br>ug cholesterol per mg cell protein | % DE NOVO | I-LDL BINDING<br>ug LDL protein per mg cell protein |
|---|---|---|---|
| none | 28.7 +/− 0.2 | 55.8 | 36.0 +/− 0.9 |
| 26-OH |  |  |  |
| 0.625 uM | 24.7 +/− 2.8 | 57.1 | 53.6 +/− 1.3 |
| 26-NH$_2$ |  |  |  |
| 0.156 uM | 30.6 +/− 3.7 | 38.3 | 40.9 +/− 3.1 |
| 0.312 uM | 25.0 +/− 0.6 | 45.1 | 43.9 +/− 4.0 |
| 0.625 uM | 28.8 +/− 1.8 | 42.0 | 52.4 +/− 8.8 |
| 26-SH |  |  |  |
| 5.0 uM | 25.5 +/− 4.3 | 49.7 | 37.8 +/− 3.4 |
| 10.0 uM | 27.4 +/− 4.0 | 47.9 | 45.8 +/− 3.9 |
| 20.0 uM | 23.2 +/− 1.2 | 41.9 | 35.7 +/− 4.8 |

These data reveal that 26-hydroxycholesterol and 26-aminocholesterol act as potent inhibitors of cholesterol synthesis, since they result in significant reductions in LDL-binding and de novo cholesterol synthesis in human fibroblasts. However, these compounds do not exhibit the same biological activity in HepG2 cells. Therefore, 26-aminocholesterol (and 26-hydroxycholesterol) appear to be selective inhibitors of serum cholesterol. They inhibit cholesterol synthesis in plasma, but do not provide a similar reduction in hepatic LDL-binding and de novo synthesis. The experiments also reveal that 26-aminocholesterol is significantly more potent, and not all reactive substitutions of 26-hydroxycholesterol are effective regulators of cholesterol production. For example, 26-thiacholesterol, which substitutes an SH-group for the NH$_2$ of 26-aminocholesterol, has no impact on either fibroblast or HepG2 LDL-binding and de novo synthesis.

Other compounds that are within the scope of the invention include substituted or unsubstituted sterols having an amino group (—NH$_2$) on any of the terminal carbons of the aliphatic side chain at position 17 of the sterol.

Thus, compounds according to the invention include the following substituted or unsubstituted sterols which are either saturated or unsaturated at carbons 5 and 6 (as shown by the dotted line).

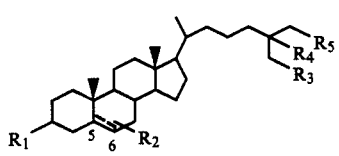

II wherein R$_1$ is one of a 3-hydroxy and 3-keto group; R$_2$ is one of hydrogen, a hydroxyl group and a keto group; and R$_3$, R$_4$, and R$_5$ are each selected from the group consisting of hydrogen and an amino group, wherein at least one of them is an amino group.

The most preferred compounds are 3-hydroxy sterols with an amino group at one or more of positions 25, 26 and 27 of the sterol. Of these, the most preferred is 26-aminocholesterol, wherein R$_2$=NH$_2$ at position 26) and R$_1$=R$_3$=methyl (CH$_3$) at positions 25 and 27.

Additional examples of compounds according to the invention and Formula II are:
25-aminocholesterol
26-aminocholesterol
27-aminocholesterol
27-nor-25-aminocholesterol
25-amino-cholesta-4,6-dien-3-one
25-amino-cholest-4-en-3-one
22-amino-cholest-5-en-3B-ol
20-amino-25,26,27-trinorcholest-5-ene-3B-ol
25-amino-cholesta-3,5-dien-7-one.

These compounds are amine-substitutions of known oxysterols that repress HMG-CoA reductase.

The finding that amino (—NH$_2$) substitution of the side chain unexpectedly enhances cholesterol inhibition in comparison to naturally occurring oxygenated or hydroxy (—OH) compounds suggests that the addition of one or more polar groups at or near the terminal end of the aliphatic side chain of a sterol will produce potent cholesterol inhibitors, since NH$_2$ is more polar than OH in this context. This is supported by the fact that thio (—SH) substitution of the side chain results in a reduction in cholesterol inhibition in comparison to both —OH and —NH$_2$, apparently because the thio group (—SH) is less polar than both the hydroxy and amino groups. Another theory is that the receptor cite for the cholesterol inhibitor compound has a higher affinity for proton acceptors, such as NH$_2$ (a base) than with OH, or with SH (an acid). Thus, contemplated equivalents of the invention would be biososteric substitutions of the compound of Formula II, wherein each —NH$_2$ group is replaced by a group that is as or more Polar or more basic than a hydroxy group.

The compounds of Formula II are either known and are available, or can be synthesized by a chemist according to known methods. For example, substitution at a terminal carbon of the sterol can be achieved by lithium aluminum hydride (LAH) reduction according to the procedure set forth above for the preparation of 26-aminocholesterol. Starting materials and intermediates are readily available or can be readily obtained, and the variations in this method that would be suitable for each substituted compound are well within the skill of an ordinary synthetic chemist. Thus, the following scheme is representative of the manner in which compounds according to the invention can be obtained:

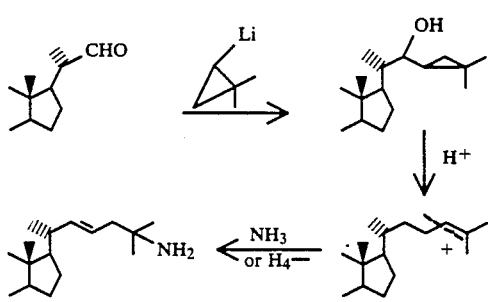

Although it is believed that the inventive compounds, and 26-aminocholesterol in particular, achieve reduced LDL-binding and cholesterol synthesis by acting as a downregulator of LDL receptors and consequently as an inhibitor of the rate-limiting enzyme HMG CoA reductase, the precise mechanism of action is not well understood, nor has the relationship between sterol structure and enzyme inhibition been fully investigated. In theory, the bioisosteric substitution of an amino group at a terminal aliphatic carbon (as in Formula II), and preferably the C-26 position of a sterol with a five carbon side chain, provides a marked increase in capacity to interact with specific configurations on a cytostolic oxysterol carrier protein that is believed to participate in the biosynthetic pathway for cholesterol production. It is also believed that observed reductions in cholesterol esterification are the result of decreased cholesterol synthesis, rather than interference with the process of esterification itself, a process which appears to be substrate driven.

Without relying on any particular theory, the potent inhibition of cholesterol synthesis observed in the present experiments suggests that the mechanisms of oxysterol metabolism cholesterol production may be different for fibroblast and hepatoblast cells, and that HMG CoA reductase may play a less significant role in hepatic cholesterol production. This reasoning is consistent with findings that HepG2 cells synthesize approteins and bile acids, and therefore hepatocytes contain sterol intermediates in bile acid synthesis that are not normally known to be present in fibroblasts. Fibroblasts and hepatocytes perform different metabolic functions, and therefore it is not unreasonable for different synthetic mechanisms and/or differing sensitivities to certain sterols to be observed.

The experiments also suggest that different synthetic mechanisms may be implicated in cell replication and turnover, which occurs frequently in the in vivo fibroblast population, as opposed to the production of cholesterol for metabolic functions in non-replicating cells, such as hepatocytes in vivo. This hypothesis is based on the fact that the present experiments measure cholesterol in cells that have reached confluent growth, meaning that the tested cultures have undergone a period of rapid cell replication, for which cholesterol is needed. Further support can be found in experiments which show that 26-aminocholesterol and other oxygenated sterols tend to downregulate DNA synthesis and cell growth through a mechanism that appears to be independent of HMG CoA reductase activity.

Whatever the mechanism of action, it has been observed that 26-aminocholesterol downregulates LDL binding and is specific for tissue cells.

Pharmaceutical Preparations

For administration to a patient, 26-aminocholesterol and other compounds of the invention can be provided as a pure compound, or as mono and di-esterified derivatives and other pharmaceutically acceptable derivatives thereof, such as mono and di-ethers. The esters can be formed using naturally occurring fatty acids, or other organic or inorganic esters can be formed using known pharmaceutically acceptable substituents can be used, such as sulfates, carbonates and glucuronides. Esterification and/or etherification can be at the 3- and/or 26- position. Aryl and/or alkyl ethers, such as methyl, ethyl or cycloalheles (e.g., cyclopentyl ethers) are also contemplated. Furthermore, acid salts and other pharmaceutically acceptable substitutions can be used.

The compounds of the present invention, (e.g., 26-aminocholesterol) are administered in amounts ranging from about 1 mg/kg to 25 mg/kg, preferably 1 to 5 mg/kg, one to three times per day. The precise dose in each instance will depend on the needs of the patient, and will be readily apparent to skilled practitioners and clinicians. Pharmaceutical preparations including the compound can be administered as a solid or liquid, or as an injectable preparation, in combination with suitable pharmaceutical carriers. Suitable pharmaceutical preparations include tablets, capsules, oral liquid and parenteral injectables and other equivalent means of administration. In a preferred embodiment, the compound is administered as a conventional solid tablet or capsule formulation using conventional diluents and excipients, such as lactose. Parenteral injections can be prepared using conventional solvents used with lipid-soluble materials, or a water-soluble salt of the sterol can be prepared.

These and other aspects and variations of the invention will be apparent to the skilled artisan. Moreover, the foregoing experiments, examples, and proposed theories of drug action are illustrative, and do not serve to limit the scope of the invention as claimed.

We claim:

1. A method for reducing the rate of cholesterol synthesis by human tissue cells which comprises administering an effective cholesterol synthesis rate-reducing amount of a sterol of the formula:

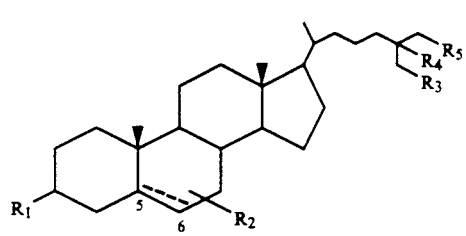

wherein
the dashed lines represent the presence of single or double bonds
$R_1$ is a 3-hydroxyl group or a 3-keto group, $R_2$ is selected from the group consisting of hydrogen, hydroxy and keto and wherein at least one of $R_3$, $R_4$ and $R_5$ is an amino group and the others are each selected from the group consisting of hydrogen and an amino group.

2. A method according to claim 1, wherein the sterol is selected from the group consisting of 25-aminocholesterol, 26-aminocholesterol, 27-aminocholesterol, 27-nor-25-aminocholesterol, 25-amino-cholesta-4,6-dien-3-one, 25-amino-cholest-4-en-3-one, and 25-amino-cholesta-3,5-dien-7-one.

3. The method of claim 2, wherein said sterol is administered in an amount ranging from about 1 to 25 mg/kg.

4. The method of claim 2, wherein 26-aminocholesterol is administered in an amount ranging from 1 to 5 mg/kg.

5. The method of claim 1, wherein said sterol is administered in combination with at least one pharmaceutically acceptable carrier.

6. The method of claim 1, wherein said sterol is administered in an amount ranging from about 1 to 25 mg/kg.

7. A method for reducing the rate of cholesterol synthesis by human tissue cells which comprises administering an effective cholesterol synthesis rate-reducing amount of 26-aminocholesterol or a pharmaceutically acceptable ester, ether, or salt thereof.

8. The method of claim 7, wherein said 26-aminocholesterol is administered in an amount ranging from about 1 to 5 mg/kg.

9. A method for reducing the rate of cholesterol accumulation in mammalian tissue cells which comprises administering a sterol of the formula:

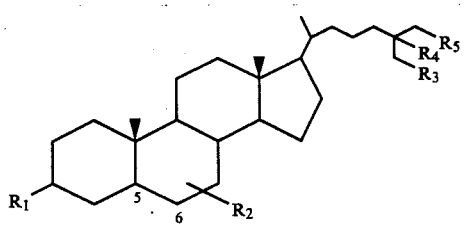

wherein the carbon atoms at positions 5 and 6 of the sterol are saturated or unsaturated, $R_1$ is a 3-hydroxyl group or a 3-keto group, $R_2$ is a hydroxyl group or a keto group, and wherein at least one of $R_3$, $R_4$ and $R_5$ is an amino group and the other are each selected from the group consisting of hydrogen and an amino group, or a fatty acid ester, a sulfate, a carbonate or a glucuronide thereof, in an amount sufficient to reduce the rate of cholesterol accumulation in the body tissue of said individual.

10. The method of claim 9, wherein said sterol is administered in combination with at least one pharmaceutically acceptable carrier.

11. The method of claim 9, wherein said sterol is administered in an amount ranging from about 1 to 25 mg/kg.

12. A method for reducing the rate of cholesterol accumulation in mammalian body tissue which comprises administering 26-aminocholesterol or a fatty acid ester, a sulfate, a carbonate or a glucuronide thereof, in an amount sufficient to reduce the rate of cholesterol accumulation in said body tissue.

13. A method for treating atherosclerosis which comprises administering a sterol of the formula:

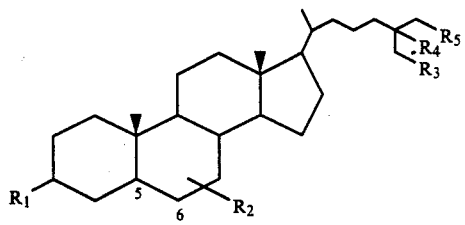

wherein the carbon atoms at positions 5 and 6 of the sterol are saturated or unsaturated, $R_1$ is a 3-hydroxyl group or a 3-keto group, $R_2$ is a hydroxyl group or a keto group, and wherein at least one of $R_3$, $R_4$ and $R_5$ is an amino group and the others are each selected from the group consisting of hydrogen and an amino group, or a fatty acid ester, a sulfate, a carbonate or a glucuronide thereof, in an amount sufficient to reduce the rate of arterial cholesterol accumulation.

14. The method of claim 13, wherein said sterol is administered in combination with at least one pharmaceutically acceptable carrier.

15. The method of claim 13, wherein said sterol is administered in an amount ranging from 1 to 5 mg/kg.

16. A method for treating atherosclerosis which comprises administering 26-aminocholesterol or a fatty acid ester, a sulfate, a carbonate or a glucuronide thereof, in an amount sufficient to reduce the rate of arterial cholesterol accumulation.

17. The method of claim 16, wherein said 26-aminocholesterol is administered in an amount ranging from 1 to 5 mg/kg.

18. A method for regulating serum cholesterol levels and preventing excessive cholesterol accumulation in human body tissues which comprises administering a sterol of the formula:

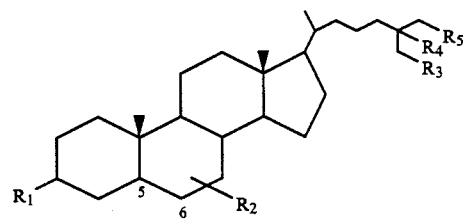

wherein the carbon atoms at positions 5 and 6 of the sterol are saturated or unsaturated, $R_1$ is a 3-hydroxyl group or a 3-keto group, $R_2$ is a hydroxyl group or a keto group, and wherein at least one of $R_3$, $R_4$ and $R_5$ is an amino group and the others are each selected from the group consisting of hydrogen and an amino group, or a fatty acid ester, a sulfate, a carbonate or a glucuronide thereof, in an amount, based on said sterol, ranging from about 1 to 25 mg/kg.

19. The method of claim 18, wherein said sterol is administered in combination with at least one pharmaceutically acceptable carrier.

20. The method of claim 18, wherein said sterol is administered in an amount ranging from 1 to 5 mg/kg.

21. A method for regulating serum cholesterol levels and preventing excessive cholesterol accumulation in human cells which comprises administering 26-aminocholesterol or a fatty acid ester, a sulfate, a carbonate, or a glucuronide thereof, in an amount, based on 26-aminocholesterol, ranging from about 1 to 25 mg/kg.

22. The method of claim 21, wherein said 26-aminocholesterol is administered in an amount ranging from 1 to 5 mg/kg.

* * * * *

UNITED STATES PATENT AND TRADEMARK OFFICE
CERTIFICATE OF CORRECTION

PATENT NO. : 4,939,134
DATED : July 3, 1990
INVENTOR(S) : Norman B. Javitt et al.

It is certified that error appears in the above-indentified patent and that said Letters Patent is hereby corrected as shown below:

IN THE TITLE PAGE

[75] Inventors, after "Stephen R. Wilson, Chatham, N.J.", insert --Emily Miao, Brighton, MA.--

Signed and Sealed this

Third Day of May, 1994

BRUCE LEHMAN

Attest:

Attesting Officer

Commissioner of Patents and Trademarks